United States Patent
Melmed et al.

(10) Patent No.: US 6,723,519 B2
(45) Date of Patent: Apr. 20, 2004

(54) COMPOSITIONS AND METHOD FOR DETERMINING THE PRESENCE OF RAT PTTG PEPTIDE IN A SAMPLE

(75) Inventors: Shlomo Melmed, Los Angeles, CA (US); Lin Pei, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 76 days.

(21) Appl. No.: 09/949,271

(22) Filed: Sep. 7, 2001

(65) Prior Publication Data

US 2002/0068716 A1 Jun. 6, 2002

Related U.S. Application Data

(62) Division of application No. 08/894,251, filed as application No. PCT/US97/21463 on Nov. 21, 1997, now Pat. No. 6,455,305.
(60) Provisional application No. 60/031,338, filed on Nov. 21, 1996.

(51) Int. Cl.[7] ............... G01N 33/53; C12Q 1/00; A61K 39/395; A61K 39/40
(52) U.S. Cl. ............... 435/7.1; 435/4; 435/7.92; 424/130.1; 424/134.1; 424/139.1; 424/141.1; 424/155.1
(58) Field of Search ............ 435/4, 7.1, 7.92; 424/130.1, 134.1, 139.1, 141.1, 155.1

(56) References Cited

FOREIGN PATENT DOCUMENTS

WO    WO 90/09442    8/1990

OTHER PUBLICATIONS

Stern, P.S., 1991, Trends in Biotechnology, vol. 9, No. 5, p. 163–169.*
Greenspan et al., 1995, Immunology Today, vol. 16, No. 5, p. 226–230.*
Marra, M. et al., "The WashU–HHMI Mouse EST project, AC W81747", EMBL Database, Jun. 27, 1996, Heidelberg, XP002066845.
Hillier, L. et al., The WashU–Merck EST project, AC AA007646, EMBL Database, Jul. 28, 1996, Heidelberg, XP002066848.
Holton, T. et al., "AC 057612", EMBL Database, Sep. 5, 1994, Heidelberg, XP002066847.
Nippon Telegraph and Telephone Corp.: "AC 075553", EMBL Database, Aug. 4, 1995, Heidelberg, XP002066848.
Gonsky, R. et al., "Transforming DNA Sequences Present in Human Prolactin–Secreting Pituitary Tumors", Molec. Endocrin., 5(11): 1687–1695, Nov. 1991.
Pei, L. Et al., "Isolation and Characterization of a Pituitary Tumor–Transforming Gene (PTTG)", Molec. Endocrin., 11(4): 433–441, Apr. 1997.
Shimon, I. et al., "Genetic Basis of Endocrine Disease", J. Clin. Endocrin. And Metab., 82(6): 1675–1681, Jun. 1997.

* cited by examiner

*Primary Examiner*—Shin-Lin Chen
(74) *Attorney, Agent, or Firm*—Pillsbury Winthrop LLP

(57) ABSTRACT

Polypeptides are expressed by the pituitary-tumor-transforming-gene (PTTG), formerly known as pituitary-tumor-specific-gene (PTSG), and nucleic acids encode them. Examples are the human and rat PTTG proteins. The nucleic acids may be applied to the production of a recombinant protein, and to the detection of the presence of PTTG genes in different species. The nucleic acids may be operatively linked to a vector, optionally provided with control and expression sequences and/or being carried by a host cell. The nucleic acids may also be delivered to a mammal to compensate for the absence, or a defective expression, of endogenous protein. The nucleic acids, proteins, and antibodies are also employed in diagnostic assays, as well as, for example, in the production of anti-PTTG antibodies (protein), therapeutic compositions and other applications of the proteins and antibodies. Various kits utilize nucleic acids, polypeptides, and/or antibodies. A transgenic non-human mammal expresses PTTG.

8 Claims, 1 Drawing Sheet

SEQUENCE LISTING

<160> NUMBER OF SEQ ID NOS: 4

<210> SEQ ID NO 1
<211> LENGTH: 974
<212> TYPE: DNA
<213> ORGANISM: Rattus rattus

<400> SEQUENCE: 1

| | | | | | |
|---|---|---|---|---|---|
| aattcggcac | gagccaacct | tgagcatctg | atcctcttgg | cttctccttc | ctatcgctga | 60 |
| gctggtaggc | tggagacagt | tgtttgggtg | ccaacatcaa | caaacgattt | ctgtagttta | 120 |
| gcgtttatga | ccctggcgtg | aagatttaag | gtctggatta | agcctgttga | cttctccagc | 180 |
| tacttctaaa | tttttgtgca | taggtgctct | ggtctctgtt | gctgcttagt | tcttccagcc | 240 |
| ttcctcaatg | ccagttttat | aatatgcagg | tctctcccct | cagtaatcca | ggatggctac | 300 |
| tctgatcttt | gttgataagg | ataacgaaga | gccaggcagc | cgtttggcat | ctaaggatgg | 360 |
| attgaagctg | ggctctggtg | tcaaagcctt | agatgggaaa | ttgcaggttt | caacgccacg | 420 |
| agtcggcaaa | gtgttcggtg | ccccaggctt | gcctaaagcc | agcaggaagg | ctctgggaac | 480 |
| tgtcaacaga | gttactgaaa | agccagtgaa | gagtagtaaa | ccctgcaat | cgaaacagcc | 540 |
| gactctgagt | gtgaaaaaga | tcaccgagaa | gtctactaag | acacaaggct | ctgctcctgc | 600 |
| tcctgatgat | gcctacccag | aaatagaaaa | gttcttcccc | ttcgatcctc | tagattttga | 660 |
| gagttttgac | ctgcctgaag | agcaccagat | ctcacttctc | cccttgaatg | gagtgcctct | 720 |
| catgatcctg | aatgaagaga | ggggcttga | gaagctgctg | cacctggacc | cccttcccc | 780 |
| tctgcagaag | cccttcctac | cgtgggaatc | tgatccgttg | ccgtctcctc | ccagcgccct | 840 |
| ctccgctctg | gatgttgaat | tgccgcctgt | ttgttacgat | gcagatattt | aaacgtctta | 900 |
| ctcctttata | gtttatgtaa | gttgtattaa | taaagcattt | gtgtgtaaaa | aaaaaaaaa | 960 |
| aaactcgaga | gtac | | | | | 974 |

<210> SEQ ID NO 2
<211> LENGTH: 199
<212> TYPE: PRT
<213> ORGANISM: Rattus rattus

<400> SEQUENCE: 2

Met Ala Thr Leu Ile Phe Val Asp Lys Asp Asn Glu Glu Pro Gly Ser
 1               5                  10                  15

Arg Leu Ala Ser Lys Asp Gly Leu Lys Leu Gly Ser Gly Val Lys Ala
            20                  25                  30

Leu Asp Gly Lys Leu Gln Val Ser Thr Pro Arg Val Gly Lys Val Phe
        35                  40                  45

Gly Ala Pro Gly Leu Pro Lys Ala Ser Arg Lys Ala Leu Gly Thr Val
    50                  55                  60

Asn Arg Val Thr Glu Lys Pro Val Lys Ser Ser Lys Pro Leu Gln Ser
65                  70                  75                  80

Lys Gln Pro Thr Leu Ser Val Lys Lys Ile Thr Glu Lys Ser Thr Lys
                85                  90                  95

Thr Gln Gly Ser Ala Pro Ala Pro Asp Asp Ala Tyr Pro Glu Ile Glu
            100                 105                 110

Lys Phe Phe Pro Phe Asp Pro Leu Asp Phe Glu Ser Phe Asp Leu Pro
        115                 120                 125

Glu Glu His Gln Ile Ser Leu Leu Pro Leu Asn Gly Val Pro Leu Met

-continued

```
                130                 135                 140
Ile Leu Asn Glu Glu Arg Gly Leu Glu Lys Leu Leu His Leu Asp Pro
145                 150                 155                 160

Pro Ser Pro Leu Gln Lys Pro Phe Leu Pro Trp Glu Ser Asp Pro Leu
                165                 170                 175

Pro Ser Pro Pro Ser Ala Leu Ser Ala Leu Asp Val Glu Leu Pro Pro
                180                 185                 190

Val Cys Tyr Asp Ala Asp Ile
                195

<210> SEQ ID NO 3
<211> LENGTH: 779
<212> TYPE: DNA
<213> ORGANISM: Homo sapiens

<400> SEQUENCE: 3
atggccgcga gttgtggttt aaaccaggag tgccgcgcgt ccgttcaccg cggcctcaga      60
tgaatgcggc tgttaagacc tgcaataatc cagaatggct actctgatct atgttgataa    120
ggaaaatgga gaaccaggca cccgtgtggt tgctaaggat gggctgaagc tggggtctgg    180
accttcaatc aaagccttag atgggagatc tcaagtttca acaccacgtt ttggcaaaac    240
gttcgatgcc ccaccagcct tacctaaagc tactagaaag ctttgggaa ctgtcaacag     300 agctacagaa aagtctgtaa agaccaaggg accctcaaa caaaaacagc caagcttttc     360
tgccaaaaag atgactgaga agactgttaa agcaaaaagc tctgttcctg cctcagatga    420
tgcctatcca gaaatagaaa aattctttcc cttcaatcct ctagactttg agagttttga    480
cctgcctgaa gagcaccaga ttgcgcacct ccccttgagt ggagtgcctc tcatgatcct    540
tgacgaggag agagagcttg aaaagctgtt tcagctgggc ccccttcac ctgtgaagat     600 gccctctcca ccatgggaat ccaatctgtt gcagtctcct tcaagcattc tgtcgaccct    660
ggatgttgaa ttgccacctg tttgctgtga catagatatt taaatttctt agtgcttcag    720
agtttgtgtg tatttgtatt aataaagcat tctttaacag ataaaaaaaa aaaaaaaa     779

<210> SEQ ID NO 4
<211> LENGTH: 202
<212> TYPE: PRT
<213> ORGANISM: Homo sapiens

<400> SEQUENCE: 4

Met Ala Thr Leu Ile Tyr Val Asp Lys Glu Asn Gly Glu Pro Gly Thr
1               5                   10                  15

Arg Val Val Ala Lys Asp Gly Leu Lys Leu Gly Ser Gly Pro Ser Ile
                20                  25                  30

Lys Ala Leu Asp Gly Arg Ser Gln Val Ser Thr Pro Arg Phe Gly Lys
            35                  40                  45

Thr Phe Asp Ala Pro Pro Ala Leu Pro Lys Ala Thr Arg Lys Ala Leu
        50                  55                  60

Gly Thr Val Asn Arg Ala Thr Glu Lys Ser Val Lys Thr Lys Gly Pro
65                  70                  75                  80

Leu Lys Gln Lys Gln Pro Ser Phe Ser Ala Lys Lys Met Thr Glu Lys
                85                  90                  95

Thr Val Lys Ala Lys Ser Ser Val Pro Ala Ser Asp Asp Ala Tyr Pro
            100                 105                 110

Glu Ile Glu Lys Phe Phe Pro Phe Asn Pro Leu Asp Phe Glu Ser Phe
        115                 120                 125
```

-continued

```
Asp Leu Pro Glu Glu His Gln Ile Ala His Leu Pro Leu Ser Gly Val
    130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Pro Trp Glu Ser
            165                 170                 175

Asn Leu Leu Gln Ser Pro Ser Ser Ile Leu Ser Thr Leu Asp Val Glu
            180                 185                 190

Leu Pro Pro Val Cys Cys Asp Ile Asp Ile
            195                 200
```

COMPOSITIONS AND METHOD FOR DETERMINING THE PRESENCE OF RAT PTTG PEPTIDE IN A SAMPLE

This application is a division of U.S. Ser. No. 08/894,251, filed Jul. 23, 1999, which issued on Sep. 24, 2002 as U.S. Pat. No. 6,455,305, and which claims priority from international application PCT/US97/21463, filed Nov. 21, 1997, which claims the priority of the filing date of U.S. Provisional Application Serial No. 60/031,338, filed Nov. 21, 1996.

The U.S. Government has a paid-up license in this invention and the right in limited circumstances to require the patent owner to license others on reasonable terms as provided for by the terms of NIH Grant No. DK42742.

BACKGROUND OF THE INVENTION

1. Field of the Invention

The present invention relates to nucleic acids and proteins encoded thereby. Invention nucleic acids encode a novel family of pituitary-tumor-specific-gene proteins. The invention also relates to methods for making and using such nucleic acids and proteins.

2. Description of the Background

Cancers and tumors are the second most prevalent cause of death in the United States, causing 450,000 deaths per year. One in three Americans will develop cancer, and one in five will die of cancer (Scientific American Medicine, part 12, I, 1, section dated 1987). While substantial progress has been made in identifying some of the likely environmental and hereditary causes of cancer, the statistics for the cancer death rate indicates a need for substantial improvement in the therapy for cancer and related diseases and disorders.

A number of cancer genes, i.e., genes that have been implicated in the etiology of cancer, have been identified in connection with hereditary forms of cancer and in a large number of well-studied tumor cells. Study of cancer genes have helped provide some understanding of the process of tumorigenesis. While a great deal more remains to be learned about cancer genes, the presently known cancer genes serve as useful models for understanding tumorigenesis.

Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

Tumor suppressor genes are genes that in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes. Examples of tumor suppression genes include, but are not limited to the retinoblastoma susceptibility gen or RB gene, the p53 gene, the deleted in colon carcinoma (DDC) gene and the neurofibromatosis type 1 (NF-1) tumor suppressor gene. Loss of function or inactivation of tumor suppressor genes may play a central role in the initiation and/or progression of a significant number of human cancers.

Anterior pituitary tumors are mostly benign hormone-secreting or non-functioning adenomas arising from a monoclonal expansion of a genetically mutated cell. Pathogenesis of tumor formation in the anterior pituitary has been intensively studied. Mechanisms for pituitary tumorigenesis involve a multi-step cascade of recently characterized molecular events. The most well characterized oncogene in pituitary tumors is gsp, a constitutively active Gs$\alpha$ resulting form activating point mutations in this gene.

Gs$\alpha$ mutations occur in about 40% of GH-secreting tumors, and constitutively activated CREB is also found in a subset of these tumors. Although the importance of GS$\alpha$ mutant proteins in the development of growth-hormone secreting pituitary tumors is well established, only about one third of these tumors contains these mutations, indicating the presence of additional transforming events in pituitary tumorigenesis. Although point mutations of Ras oncogene, loss of heterozygosity (LOH) near the Rb locus on chromosome 13, and LOH on chromosome 11 have been implicated in some pituitary tumors, the mechanism that causes pituitary cell transformation remains largely unknown. Thus, there is a need in the art for additional pituitary derived proteins that are associated with pituitary cell transformation.

SUMMARY OF THE INVENTION

The present invention relates to isolated, purified Mammalian-pituitary-Transforming-Gene (PTTG) proteins, formerly named Mammalian Pituitary-Tumor-Specific-Gene (PTSG) proteins. The PTTG proteins of the invention and fragments thereof, are useful in bioassays, as immunogens for producing anti-PTTG antibodies, or in therapeutic compositions containing such proteins and/or antibodies.

This invention also relates to a transgenic non-human mammal that expresses PTTG protein.

The present invention also relates to isolated nucleic acids encoding PTTG (PTSG) proteins of mammalian origin, such as human, rat, etc. The PTTG encoding nucleic acid is also provided in the form of a vector carrying it, as hybridizing probes\primers, in host cells carrying them, as anti-sense oligonucleotides, in DNA and RNA forms, and related compositions. The nucleic acid molecules described herein may be incorporated into expression systems known to those of skill in the art. The PTTG nucleic acids are useful as probes for assaying for the presence and/or amount of a PTTG gene or mRNA transcript in a given sample. The nucleic acid molecules described herein, and oligonucleotide fragments thereof, are also useful as primers and/or templates in a PCR reaction for amplifying genes encoding PTTG proteins.

Antibodies that are immunoreactive with invention PTTG proteins are also provided. These antibodies are useful in diagnostic assays to determine levels of PTTG proteins present in a given sample, e.g., tissue samples, biological fluids, Western blots, and the like. The antibodies can also be used to purify PUG proteins from crude cell extracts and the like. Moreover, these antibodies are considered therapeutically useful to counteract or supplement the biological effect of PTTGs in vivo.

Methods and diagnostic systems for determining the levels of PTTG protein in various tissue samples are provided as well. These diagnostic methods can be used for monitoring the level of therapeutically administered PTTG protein or fragments thereof to facilitate the maintenance of therapeutically effective amounts. These diagnostic methods can also be used to diagnose pathologic and physiological disorders that result from abnormal levels of PTTG protein.

DESCRIPTION OF THE PREFERRED EMBODIMENTS OF THE INVENTION

Figure 1:
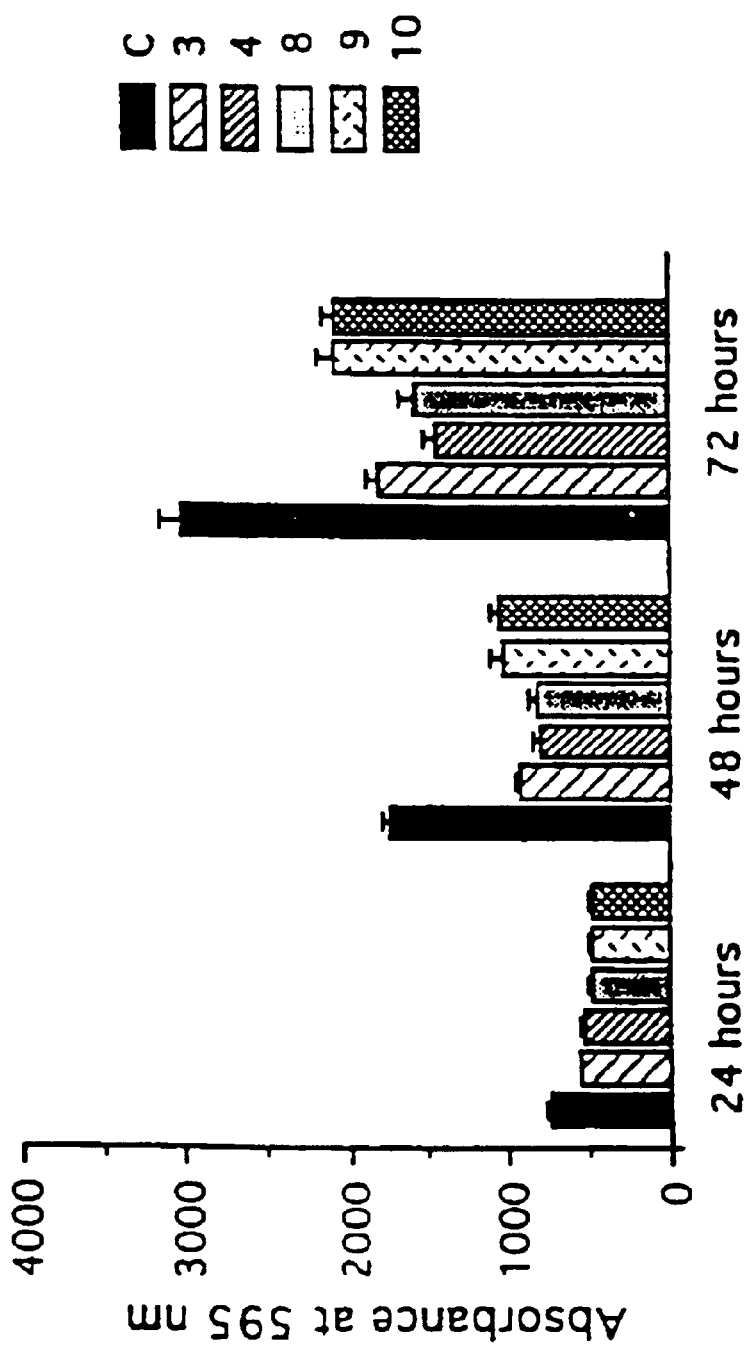
FIG. 1 shows the effect of PTTG expression on cell proliferation. The cell growth rate is expressed as absorbance at 595 nM. The error bars represent SEM (n=6). Three independent experiments were performed.

The present invention arose from a desire by the inventors to improve over the prior art methods for detection of diseases or conditions associated with overproduction of, or abnormalities in, PTTG expression. The inventors set out to isolate a PTTG gene in one species and then utilized probes based on the thus found gene sequence to probe the genomic DNA of other species, particularly human, and devise a method for mutating the PTTG gene as well as a method for replacing defective PTTG genes. They, in addition, conceived of a transgenic animal for use as a model for the study of such diseases and conditions in humans. This invention therefore provides isolated, purified mammalian pituitary-tumor-specific-gene (PTTG) proteins, polypeptides, and fragments thereof encoded by the nucleic acid of the invention. As used herein, the phrase "PTTG" refers to a mammalian family of isolated and/or substantially pure proteins, preferably human, that are able to transform cells in tissue culture, e.g., NIH 3T3 cells, and the like. The PTTG proteins of the invention have the ability to induce tumor formation in nude mice, e.g., when transfected into NIH 3T3 cells, and the like. The PTTG proteins of the invention include naturally occurring allelic variants thereof encoded by mRNA generated by alternative splicing of a primary transcript, and further include fragments which retain at least one native biological activity, such as immunogenicity.

To identify genes specifically expressed in pituitary tumor cells, the inventors utilized GH-secreting and prolactin-secreting rat pituitary tumor cell lines. In this manner, they utilized them to eliminate the admixture of normal tissues present in surgically excised human pituitary tumors and solid experimental rat tumors. Upon screening about 30% of expressed MRNA, a pituitary tumor transforming gene (PTTG) was identified and characterized. The sequence of PTTG revealed no homology to any known sequences in the GenBank. The PTTG gene encodes a protein of 199 amino acids that contains no characterized functional motif, which clearly indicates that PTTG is a novel protein.

The inventors showed the pituitary tumor specific expression of PTTG by Northern blot analysis. Other than pituitary tumor cells, testis tissue is the only normal non-tumor tissue to show PTTG expression. Interestingly, the PTTG messenger RNA in testis appears to be about 300 bp shorter than that of the pituitary tumor, which indicates that the testis messenger is a PTTG splice variant of the pituitary messenger.

The importance of PTTG in tumorigenesis is illustrated by its ability to transform 3T3 fibroblasts when overexpressed in these cells, as shown by morphological change and anchorage-independent growth of PTTG transfectants in soft agar. This finding, moreover, is underscored by the discovery that multiple tumor cell lines express abundant amounts of PTTG. Furthermore, nude mice injected with PTTG-expressing 3T3 cells developed large tumors within 3 weeks at all injection sites. These data show that PTTG alone is capable of cellular transformation without the requirement of a complimentary oncogene, and that it is potently tumorigenic in vivo. In general, full cell transformation requires two complementary oncogenes. See (Land et al, Nature, 304:696 (1983); Schwab et al., Nature, 316:160 (1985); Ruby et al., Nature 304:602 (1983). In some cases, however, the overexpression of a single oncogene may be sufficient to induce cellular transformation, as is the case in the Rat-1 cell transformation by overexpression of the Ras gene alone. See, Reynolds, V L Oncogene, 1:323 (1987). In the present case, the inventors found that PTTG does not stimulate cell proliferation in cultured transfected cells within 72 hours of assaying time. In fact, they found that PTTG unexpectedly inhibits all proliferation in cultured transfected cells. This anti-proliferative effect is similar to the potent inhibition of cell growth seen by Massague et al. with TGFβ. Once the cells are transformed, however, cell proliferation is accelerated, and rapid growth of tumors is seen in nude mice.

The PTTG proteins of this invention are polypeptides selectively bound by anti-PTTG (anti-PTSG) antibody, the antibody preferably binding to the human protein, including amino acid sequences SEQ ID NO:2, SEQ. ID No: 4, and fragments 5 to 50 amino acids long which bind to anti-PTTG antibody. The isolated PTTG proteins of the invention are generally free of other cellular components and/or contaminants normally associated with a native in vivo environment, although they may have a certain content of these products, such as proteins, RNA, DNA and polysaccharides.

The PTTG proteins are primarily, although not exclusively, expressed by pituitary tumor cells with expression detected in testis. The transcript in rat pituitary tumor cells is about 1.3 kb in size while the transcript in testis is about 1 kb, as observed by a Northern blot assay. Splice variant cDNA transcripts encoding a PTTG family of proteins are clearly also contemplated by the present invention.

Use of the terms "isolated" and/or "purified" in the present specification and claims as a modifier of DNA, RNA, polypeptide or proteins means that the DNA, RNA, polypeptide or proteins so designated have been produced in such form by the hand of man, and thus are separated from their native in vivo cellular environment. As a result of this human intervention, the recombinant DNAs, RNAs, polypeptide and proteins of the invention are useful in ways described herein that the DNAs, RNAs, polypeptide or proteins as they naturally occur are not.

As used herein, "mammalian" refers to the variety of species from which the PTTG protein of the invention is derived from, e.g., human, rat, mouse, rabbit, monkey, baboon, bovine, porcine, ovine, canine, feline, and the like. A preferred PTTG protein herein, is human PTTG.

Also part of this invention is the PTTG gene, which when defective or present, is responsible for pituitary tumorigenesis. A search of GenBank and protein profile analysis (BLAST Program search of databases of the national center for Biotechnology Information) indicated that PTTG shares no homology with known sequences, and its encoded protein is highly hydrophilic, and contains no well recognized functional motifs.

Presently preferred PTTG proteins of the invention include amino acid sequences that are substantially the same as the amino acid sequence SEQ ID NO:2, SEQ. ID No: 4, and fragments thereof about 5 to 50 amino acids long, as well as biologically active, modified forms thereof. Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as SEQ ID NO:2 therein (e.g., splice variants) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptide (or nucleic acids referred to hereinbefore) containing less than the described levels of sequence identity arising as splice variant or that are modified by conservative amino acid substitutions, or by substitution of degenerate codons are also encompassed within the scope of the present invention.

The term "biologically active" or "functional", when used herein as a modifier of the PTTG protein(s) of this invention or polypeptide fragment thereof, refers to a polypeptide that exhibits at least one of the functional characteristics attributed to PTTG. For example, one biological activity of PTTG is the ability to transform cells in vitro (e.g., NIH 3T3 cells, and the like). Yet another biological activity of PTTG is the ability to induce tumor formation in nude mice (e.g., when transfected into NIH 3T3 cells, and the like).

PTTG is also active as an immunogen for the production of polyclonal and monoclonal antibodies that bind selectively to PTTG. Thus, an invention nucleic acid encoding PTTG will encode a polypeptide specifically recognized by an antibody that also specifically recognizes the PTTG protein, preferably human, including amino acid sequences SEQ ID NO:2, SEQ. ID No: 4, and fragments thereof about 5 to 50 amino acids long which bind to anti-PTTG antibody. Such activity may be assayed by any method known to those of skill in the art. For example, a test-polypeptide encoded by a PTTG cDNA may be used to produce antibodies, which are then assayed for their ability to bind to the protein including the sequence set forth in SEQ ID NO:2. If the antibody binds to the test-polypeptide and the protein including the sequence set forth in SEQ ID NO:2 with substantially the same affinity, then the polypeptide possesses the requisite biological activity.

The PTTG proteins of the invention may be isolated by methods well-known in the art, e.g., the recombinant expression systems described herein, precipitation, gel filtration, ion-exchange, reverse-phase and affinity chromatography, and the like. Other well-known methods are described in Deutscher et al., Guide to Protein Purification: Methods in Enzymology Vol. 182, (Academic Press, (1990)), which is incorporated herein by reference. Alternatively, the isolated polypeptide of the present invention can be obtained using well-known recombinant methods as described, for example, in Sambrook et al., supra., 1989).

An example of the means for preparing the invention polypeptide(s) is to express nucleic acids encoding the PTTG in a suitable host cell, such as a bacterial cell, a yeast cell, an amphibian cell (i.e., oocyte), or a mammalian cell, using methods well known in the art, and recovering the expressed polypeptide, again using well-known methods.

The PTTG polypeptide of the invention may be isolated directly from cells that have been transformed with expression vectors as described herein. The invention polypeptide, biologically active fragments, and functional equivalents thereof can also be produced by chemical synthesis. For example, synthetic polypeptide can be produced using Applied Biosystems, Inc. Model 430A or 431A automatic peptide synthesizer (Foster City, Calif.) employing the chemistry provided by the manufacturer.

Also encompassed by the term PTTG are polypeptide fragments or polypeptide analogs thereof. The term "polypeptide analog" includes any polypeptide having an amino acid residue sequence substantially identical to a sequence specifically shown herein in which one or more residues have been conservatively substituted with a functionally similar residue and which displays the ability to mimic PTTG as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue, provided that such polypeptide displays the requisite binding activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptide of the present invention also include any polypeptide having one or more additions and/or deletions of residues, relative to the sequence of a polypeptide whose sequence is shown herein, so long as the requisite activity is maintained.

The present invention also provides compositions containing an acceptable carrier and any of an isolated, purified PTTG polypeptide, an active fragment or polypeptide analog thereof, or a purified, mature protein and active fragments thereof, alone or in combination with each other. These polypeptide or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

In accordance with another embodiment of the present invention, there are provided isolated nucleic acids, which encode the PTTG (pituitary-tumor-transforming-gene) proteins of the invention, and fragments thereof. The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of a PTTG gene or mRNA transcript in a given sample. The nucleic acid molecules described herein, and fragments thereof, are also useful as primers and/or templates in a PCR reaction for amplifying genes encoding the invention protein described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a PTTG protein. One means of isolating a nucleic acid encoding an PTTG polypeptide is to probe a mammalian genomic library with a natural or artificially designed DNA probe using methods well known in the art. DNA probes derived from the PTTG gene are particularly useful for this purpose. DNA and cDNA molecules that encode PTTG polypeptide can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an PTTG polypeptide. Such nucleic acids may include, but are not limited to, nucleic acids comprising SEQ ID NO:1, alleles thereof, preferably at least nucleotides 293–889 of SEQ ID NO:1 or splice variant cDNA sequences thereof.

As used herein, the phrases "splice variant" or "alternatively spliced", when used to describe a particular nucleotide sequence encoding an invention receptor, refers to a cDNA sequence that results from the well known eukaryotic RNA splicing process. The RNA splicing process involves the removal of introns and the joining of exons from eukaryotic primary RNA transcripts to create mature RNA molecules of the cytoplasm. Methods of isolating splice variant nucleotide sequences are well known in the art. For example, one of skill in the art may employ nucleotide probes derived from the PTTG encoding DNA of SEQ ID NO:1, SEQ. ID No: 3, alleles thereof, splice variants thereof or fragments thereof about 10 to 150 nucleotide long and their anti-sense nucleic acids to screen the cDNA or genomic library of the same or other species as described herein.

In one embodiment of the present invention, DNAs encoding the PTTG proteins of this invention comprise SEQ ID NO:1, SEQ ID No: 3, alleles thereof, splice variants thereof and fragments thereof about 15 to 150 nueleotide long and anti-sense nucleic acids thereof. In another embodiment of the present invention, DNA molecules encoding the inventive proteins comprise nucleotides 293–889 of SEQ ID NO:1, alleles thereof, splice variants thereof and fragments thereof about 10 to 150 nucleotide long. In yet another embodiment, the DNA comprises nucleotides 95–700 of SEQ ID NO:3, alleles thereof, splice variants thereof and fragments thereof about 10 to 150 nucleotides long.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2, or a larger amino acid sequence including SEQ ID NO:2. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

The present invention also encompasses nucleic acids which differ from the nucleic acids shown in SEQ ID NO:1, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptide that are the same as those disclosed herein or that have conservative amino acid variations, or that encode larger polypeptide that include SEQ ID NO:2. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding PTTG polypeptides that, by virtue of the degeneracy of the genetic code, do not necessarily hybridize to the invention nucleic acids under specified hybridization conditions. Preferred nucleic acids encoding the PTTG polypeptide of the invention comprise nucleotides encoding SEQ ID NO:2, SEQ. ID No: 4, and fragments thereof about 5 to 50 amino acids long. Exemplary nucleic acids encoding a PTTG protein of the invention may be selected from the following.

(a) DNA encoding the amino acid sequence set forth in SEQ. ID No:2, (b) DNA that hybridizes to the DNA of (a) under moderately stringent conditions, wherein said DNA encodes biologically active PTTG, or (c) DNA degenerate with respect to either (a) or (b) above, wherein said DNA encodes biologically active PTTG.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018 M NaCl at 65° C. (i.e., if a hybrid is not stable in 0.018 M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 42° C., followed by washing in 1×SSPE, 0.2% SDS, at 50° C. Denhart's solution and SSPE (see, e.g., Sambrook et al., Molecular Cloning, A Laboratory Manual, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1 or SEQ. ID No: 3, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions, i.e., typically at least 15–30 nucleotide, of SEQ ID NO:1, SEQ. ID No: 3, although longer fragments are also contemplated.

Site-directed mutagenesis of any region of PTTG cDNA is contemplated herein for the production of mutant PTTG cDNAs. For example, the Transformer Mutagenesis Kit (available from Clontech) can be used to construct a variety of missense and/or nonsense mutations to PTTG cDNA.

The inventive nucleic acids can be produced by a variety of methods well-known in the art, e.g., the methods described herein, employing PCR amplification using oligonucleotide primers from various regions of SEQ ID NO:1, and the like.

In accordance with a further embodiment of the present invention, optionally labeled PTTG-encoding cDNAs, or fragments thereof, can be employed to probe library(ies) (e.g., cDNA, genomic, and the like) for additional nucleic acid sequences encoding related novel mammalian PTTG proteins. Construction of mammalian cDNA and genomic libraries, preferably a human library, is well-known in the art. Screening of such a cDNA or genomic library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3 M sodium chloride, 0.3 M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same, i.e., similar, sequence as the coding region of the nucleic acids of the invention, preferably as nucleotides 293–889 of SEQ ID NO:1 are obtained.

As used herein, a nucleic acid "probe" is single-stranded DNA or RNA, or analogs thereof, that has a sequence of nucleotide that includes at least 14, preferably at least 20, more preferably at least 50, contiguous bases that are the same as (or the complement of) any 14 or more contiguous bases set forth in any of SEQ ID NO: 1 or SEQ. ID No: 3. Preferred regions from which to construct probes include 5' and/or 3' coding regions of SEQ ID NO:1. In addition, the entire cDNA encoding region of an invention PTTG protein, or the entire sequence corresponding to SEQ ID NO:1, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be lined to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptide, and proteins, is well known in the art. For instance, an invention antibody can be labeled by metabolic incorporation of radiolabeled amino acids provided in the culture medium. See, for example, Galfre et al., Meth. Enzymol., 73:3–46 (1981). Conventional means of protein conjugation or coupling by activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493, 795.

Also provided are antisense oligonucleotides having a sequence capable of binding specifically with any portion of an mRNA that encodes PTTG polypeptide so as to prevent translation of the mRNA. The antisense oligonucleotide may have a sequence capable of binding specifically with any portion of the sequence of the cDNA encoding PTTG polypeptide. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotide.

Compositions comprising an amount of the antisense oligonucleotide, described above, effective to reduce expression of PTTG polypeptide by passing through a cell membrane and binding specifically with mRNA encoding PTTG polypeptide so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptide. Synthetic oligonucleotides, or other antisense chemical structures are designed to bind to mRNA encoding PTTG polypeptide and inhibit translation of mRNA and are useful as compositions to inhibit expression of PTTG associated genes in a tissue sample or in a subject.

In accordance with another embodiment of the invention, kits are provided for detecting mutations, duplications, deletions, rearrangements or aneuploidies in the PTTG gene comprising at least one invention PTTG probe or antisense nucleotide.

The present invention provides means to modulate levels of expression of PTTG polypeptide by employing synthetic antisense oligonucleotide compositions (hereinafter SAOC) which inhibit translation of mRNA encoding these polypeptide. Synthetic oligonucleotides, or other antisense chemical structures designed to recognize and selectively bind to mRNA, are constructed to be complementary to portions of the PTTG coding strand or nucleotide sequences shown in SEQ. ID No: 1 or SEQ. ID No: 3. The SAOC is designed to be stable in the blood stream for administration to a subject by injection or by direct tumor site integration, or stable in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained with the sequence shown in SEQ ID NO:1. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., TIPS, 10:435 (1989) and Weintraub, Sci. American, January (1990), p.40; both incorporated herein by reference).

In accordance with yet another embodiment of the present invention, there is provided a method for the recombinant production of the PTTG protein(s) of the invention by expressing the above-described nucleic acid sequences in suitable host cells. Recombinant DNA expression systems that are suitable to produce PTTG proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome. In addition, vectors may contain appropriate packaging signals that enable the vector to be packaged by a number of viral virions, e.g., retroviruses, herpes viruses, adenoviruses, resulting in the formation of a "viral vector".

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptide, or proteins. If the polynucleic acid is derived from genomic DNA, expression may, if an appropriate eukaryotic host cell or organism is selected, include splicing of the mRNA.

Prokaryotic transformation vectors are well-known in the art and include pBlueskript and phage Lambda ZAP vectors (Stratagene, La Jolla, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., Meth. in Enzymology, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg, 1979, Nature Vol. 277:108–114) the Okayama-Berg cloning system (Mol. Cell Biol. Vol. 2:161–170, 1982), and the expression cloning vector described by Genetics Institute (Science Vol. 228:810–815, 1985), are available which provide substantial assurance of at least some expression of the protein of interest in the transformed eukaryotic cell line.

Particularly preferred base vectors which contain regulatory elements that can be linked to the invention PTTG-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., Molecular Cloning: A Laboratory Manual (2 ed.), Cold Spring Harbor Laboratory Press, Cold Spring Harbor, N.Y., USA (1989).

Exemplary methods of introducing (transducing) expression vectors containing invention nucleic acids into host cells to produce transduced recombinant cells (i.e., cells containing recombinant heterologous nucleic acid) are well-known in the art (see, for review, Friedmann, 1989, Science, 244:1275–1281; Mulligan, 1993, Science, 260:926–932, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extra-chromosomal (i.e., episomal) maintenance, or the heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., HEK293, CHO and Ltk cells), insect cells, and the like. Presently preferred host organisms are bacteria. The most preferred bacteria is *E. coli*.

In one embodiment, nucleic acids encoding the PTTG proteins of the invention may be delivered into mammalian cells, either in vivo or in vitro using suitable viral vectors well-known in the art, e.g., retroviral vectors, adenovirus vectors, and the like. In addition, where it is desirable to limit or reduce the in vivo expression of the PTTG of this invention, the introduction of the antisense strand of the invention nucleic acid is contemplated.

Viral based systems provide the advantage of being able to introduce relatively high levels of the heterologous nucleic acid into a variety of cells. Suitable viral vectors for introducing PTTG nucleic acid encoding a PTTG protein into mammalian cells (e.g., vascular tissue segments) are well known in the art. These viral vectors include, for example, Herpes simplex virus vectors (e.g., Geller et al., 1988, Science, 241:1667–1669), Vaccinia virus vectors (e.g., Piccini et al., 1987, Meth. in Enzymology, 153:545–563; Cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78–84), Moloney murine leukemia virus vectors (Danos et al., 1980, PNAS, USA, 85:6469), adenovirus vectors (e.g., Logan et al., 1984, PNAS, USA, 81:3655–3659; Jones et al., 1979, Cell, 17:683–689; Berkner, 1988, Biotechniques, 6:616–626; Cotten et al., 1992, PNAS, USA, 89:6094–6098; Graham et al., 1991, Meth. Mol. Biol., 7:109–127), adeno-associated virus vectors, retrovirus vectors, and the like. See, e.g., U.S. Pat. Nos. 4,405,712 and 4,650,764. Especially preferred viral vectors are the adenovirus and retroviral vectors.

For example, in one embodiment of the present invention, adenovirus-transferrin/polylysine-DNA (TfAdp1-DNA) vector complexes (Wagner et al., 1992, PNAS, USA, 89:6099–6103; Curiel et al., 1992, Hum. Gene Therapy, 3:147–154; Gao et al., 1993, Hum. Gene Ther., 4:14–24) are employed to transduce mammalian cells with heterologous PTTG nucleic acid. Any of the plasmid expression vectors described herein may be employed in a Tfadp1-DNA complex.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., 1988, PNAS, USA, 85:9655–9659), and the like.

In accordance with yet another embodiment of the present invention, there are provided anti-PTTG antibodies having specific reactivity with PTTG polypeptide of the present invention. Active fragments of antibodies are encompassed within the definition of "antibody". Invention antibodies can be produced by methods known in the art using the PTTG polypeptide of the invention, proteins or portions thereof as antigens. For example, polyclonal and monoclonal antibodies can be produced by methods well known in the art, as described, for example, in Harlow and Lane, Antibodies: A Laboratory Manual (Cold Spring Harbor Laboratory (1988)), which is incorporated herein by reference. The PTSG polypeptide of the invention may be utilized as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., Trends Pharmacol. Sci. 12:338 (1991); Ausubel et al., Current Protocols in Molecular Biology (John Wiley and Sons, NY (1989) which are incorporated herein by reference).

Antibody so produced can be used, inter alia, in diagnostic methods and systems to detect the level of PTTG protein present in a mamma, preferably human, body sample, such as tissue or vascular fluid. Such antibodies can also be used for the immunoaffinity or affinity chromatography purification of the PTTG protein of the invention. In addition, methods are contemplated herein for detecting the presence of PTTG polypeptide either on the surface of a cell or within a cell (such as within the nucleus), which methods comprise contacting the cell with an antibody that specifically binds to PTTG polypeptide, under conditions permitting binding of the antibody to PTTG polypeptide, detecting the presence of the antibody bound to PTTG, and thereby detecting the presence of invention polypeptide on the surface of, or within, the cell. With respect to the detection of such polypeptide, the antibodies can be used for in vitro diagnostic or in vivo imaging methods.

Immunological procedures useful for in vitro detection of target PTTG polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

The anti-PTTG antibodies of the invention modulate activity of the PTTG polypeptide in living animals, in humans, or in biological tissues or fluids isolated therefrom. Accordingly, compositions comprising a carrier and an amount of an antibody having specificity for PTTG polypeptide effective to block naturally occurring ligands or other PTTG-binding proteins from binding to invention PTTG polypeptide are contemplated herein. For example, a monoclonal antibody directed to an epitope of PTTG polypeptide molecules present on the surface of a cell and having an amino acid sequence substantially the same as an amino acid sequence for a cell surface epitope of an PTTG polypeptide including the amino acid sequence shown in SEQ ID NO:2, SEQ. ID No: 4, and fragments thereof, may be useful for this purpose.

The present invention further provides transgenic non-human mammals that are capable of expressing exogenous nucleic acids encoding PTTG polypeptide. As employed herein, the phrase "exogenous nucleic acid" refers to nucleic acid sequence which is not native to the host, or which is present in the host in other than its native environment (e.g., as part of a genetically engineered DNA construct). In addition to naturally occurring levels of PTTG, the PTTG proteins of this invention may either be overexpressed, underexpressed, or expressed in an inactive mutated form, such as in the well-known knock-out transgenics, in transgenic mammals.

Also provided are transgenic non-human mammals capable of expressing nucleic acids encoding PTTG polypeptide so mutated as to be incapable of normal activity, i.e., do not express native PTTG. The present invention also provides transgenic non-human mammals having a genome comprising antisense nucleic acids complementary to nucleic acids encoding PTTG polypeptide, placed so as to be transcribed into antisense mRNA complementary to mRNA encoding PTTG polypeptide, which hybridizes to the mRNA and, thereby, reduces the translation thereof. The nucleic acid may additionally comprise an inducible promoter and/ or tissue specific regulatory elements, so that expression can be induced, or restricted to specific cell types. Examples of nucleic acids are DNA or cDNA having a coding sequence substantially the same as the coding sequence shown in SEQ ID NO:1. An example of a non-human transgenic mammal is a transgenic mouse.

Animal model systems which elucidate the physiological and behavioral roles of PTTG polypeptide are also provided, and are produced by creating transgenic animals in which the expression of the PTTG polypeptide is altered using a variety of techniques. Examples of such techniques include the insertion of normal or mutant versions of nucleic acids encoding an PTTG polypeptide by microinjection, retroviral infection or other means well known to those skilled in the art, into appropriate fertilized embryos to produce a transgenic animal. (See, for example, Hogan et al., Manipulating the Mouse Embryo: A Laboratory Manual (Cold Spring Harbor Laboratory, (1986)).

Also contemplated herein, is the use of homologous recombination of mutant or normal versions of PTTG genes with the native gene locus in transgenic animals, to alter the regulation of expression or the structure of PTTG polypeptide (see, Capecchi et al., Science 244:1288 (1989); Zimmer et al., Nature 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of PTTG polypeptide.

In contrast to homologous recombination, microinjection adds genes to the host genome, without removing host genes. Microinjection can produce a transgenic animal that is capable of expressing both endogenous and exogenous PTTG protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptide and combinations thereof, as well as antibodies of the present invention, can be used to screen compounds in vitro to determine whether a compound functions as a potential agonist or antagonist to the PTTG polypeptide of the invention. These in vitro screening assays provide information regarding the function and activity of the PTTG polypeptide of the invention, which can lead to the identification and design of compounds that are capable of specific interaction with one or more types of polypeptide, peptides or proteins.

In accordance with still another embodiment of the present invention, there is provided a method for identifying compounds which bind to PTTG polypeptide. The invention proteins may be employed in a competitive binding assay. Such an assay can accommodate the rapid screening of a large number of compounds to determine which compounds, if any, are capable of binding to PTTG proteins. Subsequently, more detailed assays can be carried out with those compounds found to bind, to further determine whether such compounds act as modulators, agonists or antagonists of invention proteins.

In another embodiment of the invention, there is provided a bioassay for identifying compounds which modulate the activity of the PTTG polypeptide of the invention. According to this method, the PTTG polypeptides of the invention are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for PTTG polypeptide.

In accordance with another embodiment of the present invention, transformed host cells that recombinantly express the PTSG polypeptide of the invention may be contacted with a test compound, and the modulating effect(s) thereof can then be evaluated by comparing the PTTG-mediated response (e.g., via reporter gene expression) in the presence and absence of test compound, or by comparing the response of test cells or control cells (i.e., cells that do not express PTTG polypeptide), to the presence of the compound.

As used herein, a compound or a signal that "modulates the activity" of PTTG polypeptide of this invention refers to a compound or a signal that alters the activity of PTTG polypeptide so that the activity of the invention PTTG polypeptide is different in the presence of the compound or signal than in the absence of the compound or signal. In particular, such compounds or signals include agonists and antagonists. An agonist encompasses a compound or a signal that activates PTTG protein function. Alternatively, an antagonist includes a compound or signal that interferes with PTTG protein function. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate PTTG activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of PTTG polypeptide can be modulated by contacting the polypeptide with an effective amount of at least one compound identified by the above-described bioassays.

In accordance with another embodiment of the present invention, there are provided methods for diagnosing or detecting a pathological mass (such as, for example, an endocrine or non-endocrine tumor, atherosclerotic plaque, and the like), said method comprising detecting, in cells of a subject, a transcribed or mutant sequence including SEQ ID NO:1.

In a particular embodiment, the invention diagnostic methods described herein are useful for differential diagnosis of malignant versus benign tumors in biopsy specimens, and the like. In another embodiment, the invention diagnostic methods described herein are useful for predicting tumor behavior and responsiveness to therapy.

In accordance with another embodiment of the present invention, there are provided methods for diagnosing pituitary tumors, said method comprising detecting, in pituitary-derived cells of a subject, a transcribed mRNA sequence including SEQ ID NO:1.

In accordance with another embodiment of the present invention, there are provided diagnostic systems, preferably in lit form, comprising at least one invention nucleic acid in a suitable packaging material. The diagnostic nucleic acids are derived from the PTTG-encoding nucleic acids described herein. In one embodiment, for example, the diagnostic nucleic acids are derived from SEQ ID NO:1. Invention diagnostic systems are useful for assaying for the presence or absence of nucleic acid encoding PTTG in either genomic DNA or in transcribed nucleic acid (such as mRNA or cDNA) encoding PTTG in any tumors (e.g., pituitary, and the like) or diseased tissue. Invention diagnostic systems contemplated herein, may make use of well-known polymerase chain reaction (PCR) or RTPCR (reverse-transcriptase-PCR) methodologies.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding PTTG including the nucleotide sequence set forth in SEQ ID NO:1 or a mutant thereof, thereby diagnosing the presence of, or a predisposition for, a particular pathology (such as, for example, pituitary tumorigenesis, and the like). In addition, the packaging material contains instructions indicating how the materials within the kit are employed both to detect a particular sequence and diagnose the presence of, or a predisposition for, a particular pathology.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All US patents and all publications mentioned herein are incorporated in their entirety by reference thereto. The invention will now be described in greater detail by reference to the following non-limiting examples.

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y. USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987).

EXAMPLES

Example 1

Isolation of PTTG cDNA

To clarify the molecular mechanisms involved in pituitary tumorigenesis, differential display PCR was used to identify mRNAs differentially expressed in pituitary tumor cells (see, e.g., Risinger et al., 1994, Molec. Carcinogenesis, 11:13–18; and Qu et al., 1996, Nature, 380:243–247). GC and $GH_4$ pituitary tumor cell lines (ATCC #CCL-82 and #CCL-82.1, respectively) and an osteogenic sarcoma cell line UM108 (ATCC #CRL-1663) were grown in DMEM supplemented with 10% fetal bovine serum. Normal Sprague-Dawley rat pituitaries were freshly excised. Total RNA was extracted from tissue cultured cells and pituitary tissue using RNeasy™ kit (Qiagen) according to manufacturer's instructions. Trace DNA contamination in RNA preparations was removed by DNase1 (GenHunter Corporation) digestion. cDNA was synthesized from 200 ng total RNA using MMLV reverse transcriptase (GenHunter Corporation), and one of the three anchored primers (GenHunter Corporation). The cDNA generated was used in the PCR display.

Three downstream anchored primers $AAGCT_{11}N$ (where "N" may be A, G, or C; SEQ ID NO:7), were used in conjunction with 40 upstream arbitrary primers for PCR display. 120 primer pairs were used to screen mRNA expression in pituitary tumors versus normal pituitary. One tenth of the cDNA generated from the reverse transcriptase reaction was amplified using AmpliTaq DNA polymerase (Perkin Elmer) in a total volume of 20 $\mu$l containing 10 mM Tris, pH 8.4, 50 nM KCl, 1.5 mM $MgCl_2$, 0.001% gelatin, 2 $\mu$M dNTPs, 0.2 $\mu$M each primer and 1 $\mu$l [$^{35}$S]dATP. PCR cycles consisted of 30 seconds at 94° C., 2 minutes at 40° C., and 30 seconds at 72° C. for 40 cycles. The products separated on 6% sequencing gels, and dried gels were exposed to Kodak film for 24 to 48 hours.

After development, DNA fragments amplified from pituitary tumor and normal pituitary were compared. Bands unique to pituitary tumor were excised from the gel, and DNA extracted by boiling in 100 $\mu$l water and precipitated with ethanol in the presence of glycogen (GenHunter Corporation). DNA was reamplified using the original set of primers and the same thermal cycling conditions except that the dNTP concentration was increased to 20 $\mu$M. Reaction products were run on 1% agarose gel and stained with ethidium bromide. Bands were excised from the gel, eluted (Qiagen), cloned in to TA vectors (Invitrogen) and sequenced using sequenase (USB). Using 120 primer pairs in the above-described PCR assay, 11 DNA bands that appeared to be differentially expressed in pituitary tumor cells were identified. These bands were evaluated further by Northern blot analysis, using the PCR products as probes.

For Northern blot analysis, 20 $\mu$g of total RNA were fractionated on 1% agarose gel, blotted on to nylon membrane and hybridized with random primed probe using Quickhyb solutions (Stratagene). After washing, membranes were exposed to Kodak films for 6 to 72 hours. As a result of the Northern blot assay, pituitary tumor specific signals were detected for 2 bands. DNA sequence analysis revealed that one sequence was homologous with Insulin-induced growth response protein, while the another 396 base pair fragment (amplified using 5' AAGCTTTTTTTTTTG 3' [SEQ ID NO:5] as the anchored primer and 5' AAGCTTGCTGCTC 3' [SEQ ID NO:6] as an arbitrary primer) showed no homology to known sequences in the GenBank. This 396 bp fragment detected a highly expressed mRNA of about 1.3 kb in pituitary tumor cells, but not in normal pituitary nor in osteogenic sarcoma cells.

Example 2

Characterization of PTTG cDNA

To characterize this pituitary tumor-specific mRNA further, a cDNA library was constructed using mRNA isolated from rat pituitary tumor cells. Poly A+RNA was isolated from pituitary tumor $GH_4$ cells using messenger RNA isolation kit (Stratagene) according to manufacturer's instructions, and was used to construct a cDNA library in ZAP Express vectors (Stratagene). The cDNA library was constructed using ZAP Express™ cDNA synthesis and Gigapack III gold cloning kit (Stratagene) following manufacturer's instructions. The library was screened using the 396 bp differentially displayed PCR product (cloned into TA vector) as the probe. After tertiary screening, positive clones were excised by in vivo excision using helper phage. The resulting pBK-CMV phagemid containing the insert was identified by Southern Blotting analysis. Unidirectional nested deletions were made into the DNA insert using EXOIII/Mung bean nuclease deletion kit (Stratagene) following manufacturer's instructions. Both strands of the insert DNA were sequenced using Sequenase (USB).

Using the 396 bp PCR fragment described in Example 1 as a probe, a cDNA clone of 974 bp was isolated and characterized. This cDNA was designated as pituitary-tumor-transforming gene (PTTG). The sequence of PTTG contains an open reading frame for 199 amino acids (SEQ ID NO:2). The presence of an in-frame stop codon upstream of the predicted initiation codon indicates that PTTG contains the complete ORF. The nucleic acid and protein sequences are provided in Table 1 below.

TABLE 1

PTTG Nucleic Acid and Protein Sequences

```
AATTCGGCAC GAGCCAACCT TGAGCATCTG ATCCTCTTGG CTTCTCCTTC CTATCGCTGA        60

GCTGGTAGGC TGGAGACAGT TGTTTGGGTG CCAACATCAA CAAACGATTT CTGTAGTTTA       120

GCGTTTATGA CCCTGGCGTG AAGATTTAAG GTCTGGATTA AGCCTGTTGA CTTCTCCAGC       180

TACTTCTAAA TTTTTGTGCA TAGGTGCTCT GGTCTCTGTT GCTGCTTAGT TCTTCCAGCC       240

TTCCTCAATG CCAGTTTTAT AATATGCAGG TCTCTCCCCT CAGTAATCCA GG ATG           295
                                                          Met
                                                           1

GCT ACT CTG ATC TTT GTT GAT AAG GAT AAC GAA GAG CCA GGC AGC CGT         343
Ala Thr Leu Ile Phe Val Asp Lys Asp Asn Glu Glu Pro Gly Ser Arg
             5                  10                  15

TTG GCA TCT AAG GAT GGA TTG AAG CTG GGC TCT GGT GTC AAA GCC TTA         391
Leu Ala Ser Lys Asp Gly Leu Lys Leu Gly Ser Gly Val Lys Ala Leu
         20                  25                  30

GAT GGG AAA TTG CAG GTT TCA ACG CCA CGA GTC GGC AAA GTG TTC GGT         439
Asp Gly Lys Leu Gln Val Ser Thr Pro Arg Val Gly Lys Val Phe Gly
     35                  40                  45

GCC CCA GGC TTG CCT AAA GCC AGC AGG AAG GCT CTG GGA ACT GTC AAC         487
Ala Pro Gly Leu Pro Lys Ala Ser Arg Lys Ala Leu Gly Thr Val Asn
 50              55                  60                      65

AGA GTT ACT GAA AAG CCA GTG AAG AGT AGT AAA CCC CTG CAA TCG AAA         535
Arg Val Thr Glu Lys Pro Val Lys Ser Ser Lys Pro Leu Gln Ser Lys
             70                  75                  80

CAG CCG ACT CTG AGT GTG AAA AAG ATC ACC GAG AAG TCT ACT AAG ACA         583
Gln Pro Thr Leu Ser Val Lys Lys Ile Thr Glu Lys Ser Thr Lys Thr
             85                  90                  95

CAA GGC TCT GCT CCT GCT CCT GAT GAT GCC TAC CCA GAA ATA GAA AAG         631
Gln Gly Ser Ala Pro Ala Pro Asp Asp Ala Tyr Pro Glu Ile Glu Lys
         100                 105                 110

TTC TTC CCC TTC GAT CCT CTA GAT TTT GAG AGT TTT GAC CTG CCT GAA         679
Phe Phe Pro Phe Asp Pro Leu Asp Phe Glu Ser Phe Asp Leu Pro Glu
     115                 120                 125

GAG CAC CAG ATC TCA CTT CTC CCC TTG AAT GGA GTG CCT CTC ATG ATC         727
Glu His Gln Ile Ser Leu Leu Pro Leu Asn Gly Val Pro Leu Met Ile
130                 135                 140                 145

CTG AAT GAA GAG AGG GGG CTT GAG AAG CTG CTG CAC CTG GAC CCC CCT         775
Leu Asn Glu Glu Arg Gly Leu Glu Lys Leu Leu His Leu Asp Pro Pro
                 150                 155                 160

TCC CCT CTG CAG AAG CCC TTC CTA CCG TGG GAA TCT GAT CCG TTG CCG         823
Ser Pro Leu Gln Lys Pro Phe Leu Pro Trp Glu Ser Asp Pro Leu Pro
             165                 170                 175

TCT CCT CCC AGC GCC CTC TCC GCT CTG GAT GTT GAA TTG CCG CCT GTT         871
Ser Pro Pro Ser Ala Leu Ser Ala Leu Asp Val Glu Leu Pro Pro Val
             180                 185                 190

TGT TAC GAT GCA GAT ATT TAAACGTCTT ACTCCTTTAT AGTTTATGTA                919
Cys Tyr Asp Ala Asp Ile                                           (SEQ ID NO:2)
     195                 200

AGTTGTATTA ATAAAGCATT TGTGTGTAAA AAAAAAAAA AAAACTCGAG AGTAC            974
                                                                  (SEQ ID NO:1)
```

This was verified by demonstrating both in vitro transcription and in vitro translation of the gene product as described in Example 3.

Example 3
In Vitro Transcription & Translation of PTTG

Sense and antisense PTTG mRNAs were in vitro transcribed using T3 and T7 RNA polymerase (Stratagene), respectively. The excess template was removed by DNase I digestion. The in vitro transcribed mRNA was translated in rabbit reticular lysate (Stratagene). Reactions were carried out at 30° C. for 60 minutes, in a total volume of 25 µl containing 3 µl in vitro transcribed RNA, 2 µl $^{35}$S-Methionine (Dupond) and 20 µl lysate. Translation products were analyzed by SDS-PAGE (15% resolving gel and 5% stacking gel), and exposed to Kodak film for 16 hours.

The results indicate that translation of in vitro transcribed PTTG sense mRNA results in a protein of approximately 25 KD on SDS-PAGE, whereas no protein was generated in either the reaction without added mRNA or when PTTG antisense mRNA was utilized.

Example 4
Expression of PTTG mRNA

A search of GenBank and a protein profile analysis (using a BLAST Program search of databases of the national center for Biotechnology Information) indicated that PTTG shares no homology with known sequences, and its encoded protein is highly hydrophilic, and contains no well recognized functional motifs. The tissue expression patten of PTTG mRNA was studied by Northern Blot analysis. A rat multiple tissue Northern blot was purchased from Clontech. Approximately 2 μg of poly A+RNA per lane from eight different rat tissues (heart, brain, spleen, lung, liver, skeletal muscle, kidney, and testis) was run on a denaturing formaldehyde 1.2% agarose gel, transferred to nylon membrane and UV-cross linked. The membrane was first hybridized to the full length PTTG cDNA probe, and was stripped and rehybridized to a human β-actin cDNA control probe. Hybridization was performed at 60° C. for one hour in ExpressHyb hybridization solution (Clontech). Washing was twice 15 minutes at room temperature in 2×SSC, 0.05% SDS, and twice 15 minutes at 50° C. in 0.1% SSC, 0.1% SDS. Exposure time for PTTG probe was 24 hrs, and actin probe 2 hours.

The results of the Northern assay indicate that testis is the only tissue, other than pituitary tumor cells, that expresses PTTG mRNA, and the testis expression level is much lower (2 μg polyA+mRNA, 24 hour exposure) than in pituitary tumor cells (20 μg total RNA, 6 hour exposure). Interestingly, the testicular transcript (about 1 Kb) is shorter than the transcript in pituitary tumors (1.3 Kb), indicating that the mRNA is differentially spliced in testis, and that the 1.3 Kb transcript is specific for pituitary tumor cells.

Example 5
Over-expression of PTTG by NIH 3T3 Fibroblast Cells

Since PTTG mRNA is over-expressed in pituitary tumor cells, whether this protein exerts an effect on cell proliferation and transformation was determined. An eukaryotic expression vector containing the entire coding region of PTTG was stably transfected into NIH 3T3 fibroblasts.

The entire coding region of the PTTG was cloned in frame into pBK-CMV eukaryotic expression vector (Stratagene), and transfected into NIH 3T3 cells by calcium precipitation. 48 hrs after transfection, cells were diluted 1:10 and grown in selection medium containing 1 mg/ml G418 for two weeks in when individual clones were isolated. Cell extracts were prepared from each colony and separated on 15% SDS-polyacrylamide gels, and blotted onto nylon membrane. A polyclonal antibody was generated using the first 17 amino acids of PTTG as epitope (Research Genetics). The antibody was diluted 1:5000 and incubated with the above membrane at room temperature for 1 hour. After washing, the membrane was incubated with horseradish peroxidase-labeled secondary antibody for one hour at room temperature. The hybridization signal was detected by enhanced chemiluminescence (ECL detection system, Amersham).

Expression levels of the PTTG were monitored by immunoblot analysis using the above-described specific polyclonal antibody directed against the first 17 amino acids of the protein. Expression levels of individual clones varied, and clones that expressed higher protein levels were used for further analysis.

Example 6
Effect of PTTG Expression on Cell Proliferation

A nonradioactive cell proliferation assay was used to determine the effect of PTTG protein over-expression on cell proliferation (see, e.g., Mosmann, T., 1983, J. Immunol. Meth., 65:55–63; and Carmichael et al., 1987, Cancer Res., 47:943–946). Cell proliferation was assayed using CellTiter 96™ Non-radioactive cell proliferation Assay kit (Promega) according to the manufacturer's instructions. Five thousand cells were seeded in 96 well plates (6 wells for each clone in each assay), and incubated at 37° C. for 24 to 72 hours. At each time point, 15 μl of the Dye solution were added to each well, and incubated at 37° C. for 4 hours. One hundred μl of the solubilization/stop solution were then added to each well. After one hour incubation, the contents of the wells were mixed, and absorbance at 595 nm was recorded using an ELISA reader. Absorbance at 595 nm correlates directly with the number of cells in each well.

Three independent experiments were performed and the results are shown in FIG. 1. In FIG. 1, the cell growth rate is expressed as absorbance at 595 nM. The error bars represent SEM (n=6). The results (FIG. 1) show that the growth rate of 3T3 cells expressing PTTG protein (assayed by cellular conversion of tetrazolium into formazan) was suppressed 25 to 50% as compared with 3T3 cells expressing the pCMV vector alone, indicating that PTTG protein inhibits cell proliferation.

Example 7
PTTG Induction of Morphological Transformation and Soft-agar Growth of NIH 3T3 Cells The transforming property of PTTG protein was demonstrated by its ability to form foci in monolayer cultures and show anchorage-independent growth in soft agar, as shown in Table 2 below.

TABLE 2

Colony Formation by NIH 3T3 Cells Transfected with PTTG cDNA Constructs

| Cell line | Growth in Soft Agar | Efficiency of Colony formation in Soft Agar (%) |
|---|---|---|
| No DNA | 0 | 0 |
| Vector only | 1.3 ± 0.7 | 0.013 |
| PTTG 3 | 26 ± 4.6 | 0.26 |
| PTTG 4 | 132 ± 26 | 1.32 |
| PTTG 8 | 33 ± 6.0 | 0.33 |
| PTTG 9 | 72 ± 13 | 0.72 |
| PTTG 10 | 92 ± 18 | 0.92 |

$10^4$ cells/dish were plated as described in FIG. 7.
Plates were scored at 14 days.
Only colonies consist of at least 40 cells were counted.
Values are means ± SEM of triplicates.
Efficiency of colony formation was calculated as percentage of number of colonies divided by total number of cells.

As primary pituitary cells are an admixture of multiple cell types and they do not replicate in vitro, NIH 3T3 cells were employed. For the soft agar assay, 60 mm tissue culture plates were coated with 5 ml soft-agar (20% 2×DMEM, 50% DMEM, 10% fetal bovine serum, 20% 2.5% agar, melted and combined at 45° C.). See, Schwab et al., 1985, Nature, 316:160–162. 2 ml cells suspended in medium were then combined with 4 ml agar mixture, and 1.5 ml of this mixture added to each plate. The cells were plated at a density of $10^4$ cells/dish and incubated for 14 days before counting the number of colonies and photography.

The results indicate that NIH 3T3 parental cells and 3T3 cells transfected with pCMV vector do not form colonies on soft agar, whereas 3T3 cells transfected with PTTG form large colonies. In addition, focal transformation is observed in cells over-expressing PTTG protein, but cells expressing pCMV vector without the PTTG insert showed similar morphology to the parental 3T3 cells.

Example 8
Determination of in vivo PTTG Tumorigenicity

To determine whether PTTG is tumorigenic in vivo, PTTG-transfected 3T3 cells were injected subcutaneously into athymic nude mice. $3 \times 10^5$ cells of either PTTG or pCMV vector alone transfected cells were resuspended in PBS and injected subcutaneously into nude mice (5 for each group). Tumors were excised from animals at the end of the 3rd week and weighted. All injected animals developed large tumors (1–3 grams) within 3 weeks. The results are shown in Table 3 below. No mouse injected with vector only transfected cells developed tumors.

TABLE 3

In vivo Tumorigenesis by NIH 3T3 Cells
Transfected with PTTG cDNA Expression Vector

| Cell line | Animals injected | Tumor formation |
|---|---|---|
| Vector only | 5 | 0/5 |
| PTTG 4 | 5 | 5/5 |

$3 \times 10^5$ cells were injected subcutaneously into athymic nude mice.
Tumors developed within 3 weeks and weighed 1–3 grams at sacrifice.

These results clearly indicate that PTTG is a potent transforming gene in vivo.

Example 9
Human Carcinoma Cell Lines Express PTTG

The expression of PTTG in various human cell lines was studied employing a multiple human cancer cell line Northern blot (Clontech). The specific cell lines tested are shown in Table 4 below.

TABLE 4

Human Carcinoma Cell Lines Tested

| | Cell Line | PTTG Expression |
|---|---|---|
| 1 | Promyelocytic Leukemia HL-60 | + |
| 2 | HeLa Cell S3 | + |
| 3 | Chronic Myelogenous Leukemia K-562 | + |
| 4 | Lymphoblastic Leukemia MOLT-4 | + |
| 5 | Burkitt's lymphoma Raji | + |
| 6 | Colorectal Adenocarcinoma SW 480 | + |
| 7 | Lung Carcinoma A549 | + |
| 8 | Melanoma G361 | + |

About 2 μg polyA RNA from each of the 8 cell lines indicated in Table 1 above were placed on each lane of a denaturing formaldehyde 1.2% agarose gel, separated by denaturing gel electrophoresis to ensure intactness, transferred to a charge-modified nylon membrane by Northern blotting, and fixed by UV irradiation. Lanes 1 to 8 contained RNA from promyelocytic leukemia HL-60, HeLa cell line S3, human chronic myelogenous leukemia K-562, lymphoblastic leukemia MOLT-4, Burkitt's lymphoma Raji, colorectal adenocarcinoma SW 480, lung carcinoma A549 and melanoma G361, respectively. RNA size marker lines at 9.5, 7.5, 4.4, 2.4, and 1.35 kb were indicated in ink on the left margin of the blot, and utilized as sizing standards, and a notch was cut out from the lower left hand corner of the membrane to provide orientation. Radiolabeled human β-actin cDNA was utilized as a control probe for matching of different batches of polyA RNAs. A single control band at 2.0 kb in all lanes spotted is confirmatory.

The blots were probed with the full length rat PTTG cDNA probe (SEQ ID No: 1; 974 bp) at 60° C. for 1 hr. in ExpressHyb hybridization solution (Clontech) as described by Sambrook et al., the relevant section of which reference is incorporated herein by reference. See, Sambrook et al., Molecular Cloning: A Laboratory Manual, 2nd. Ed, Cold Spring Harbor Laboratory Press, Cold Spring Harbor, N.Y. (1989). The blots were then washed twice for 15 min at room temperature in 2×SSC, 0.05% SDS, and twice for 15 min at 50° C. in 0.1% SSC, 0.1% SDS. A more detailed description of the remaining experimental procedures masy be found in Pei & Melmed, the relevant section of which is incorporated herein by reference. See, Pei & Melmed, Endocrinology 4:433–441 (1997).

All cells tested by the Northern blot analysis as described above evidenced expression of human PTTG, including lymphoma, leukemia, melanoma and lung carcinomas, among others.

Example 10
Cloning of Human PTTG cDNA

A human fetal liver cDNA library (Clontech, Palo Alto, Calif.) was screened as described by Maniatis et al. using a radioactively labeled cDNA fragment of the entire rat PTTG coding region as a probe. See, Maniatis et al, Molecular cloning, Cold Spring Harbor Press, 1989. The cDNA inserts from positive clones were subcloned into plasmid pBluescript-SK (Stratagene, La Jolla, Calif.), and subjected to sequence analysis using Sequenase kit (U.S. Biochemical Corp., Cleveland, Ohio). The sequence of the nucleic acid is provided in Table 5 below.

TABLE 5

PTTG Nucleic Acid Sequences

1 ATGGCCGCGA GTTGTGGTTT AAACCAGGAG TGCCGCGCGT CCGTTCACCG

51 CGGCCTCAGA TGAATGCGGC TGTTAAGACC TGCAATAATC CAGA<u>ATG GCT</u>

101 <u>ACT CTG ATC TAT GTT GAT AAG GAA AAT GGA GAA CCA GGC ACC</u>

123 <u>CGT GTG GTT GCT AAG GAT GGG CTG AAG CTG GGG TCT GGA CCT</u>

185 <u>TCA ATC AAA GCC TTA GAT GGG AGA TCT CAA GTT TCA ACA CCA</u>

TABLE 5-continued

PTTG Nucleic Acid Sequences

207 CGT TTT GGC AAA ACG TTC GAT GCC CCA CCA GCC TTA CCT AAA

249 GCT ACT AGA AAG GCT TTG GGA ACT GTC AAC AGA GCT ACA GAA

311 AAG TCT GTA AAG ACC AAG GGA CCC CTC AAA CAA AAA CAG CCA

350 CCA AGC TTT TCT GCC AAA AAG ATG ACT GAG AAG ACT GTT AAA

392 GCA AAA AGC TCT GTT CCT GCC TCA GAT GAT GCC TAT CCA GAA

334 ATA GAA AAA TTC TTT CCC TTC AAT CCT CTA GAC TTT GAG AGT

376 TTT GAC CTG CCT GAA GAG CAC CAG ATT GCG CAC CTC CCC TTG

419 AGT GGA GTG CCT CTC ATG ATC CTT GAC GAG GAG AGA GAG CTT

560 GAA AAG CTG TTT CAG CTG GGC CCC CCT TCA CCT GTG AAG ATG

602 CCC TCT CCA CCA TGG GAA TCC AAT CTG TTG CAG TCT CCT TCA

644 AGC ATT CTG TCG ACC CTG GAT GTT GAA TTG CCA CCT GTT TGC

686 TGT GAC ATA GAT ATT TAA

704    ATTTCTT AGTGCTTCAG AGTTTGTGTG TATTTGTATT AATAAAGCAT

751 TCTTTAACAG ATAAAAAAAA AAAAAAAA (SEQ. ID No:3)

The open reading frame of 606 bp is indicated by underlining.

A complete open reading frame containing 606 bp was found in the positive clones. The homology between the nucleotide sequences of the open reading frame and the coding region of rat PTTG or PTSG (old nomenclature) is 85%. The deduced amino acid sequence is shown in Table 6 below.

TABLE 6

PTTG Amino Acid Sequence

1    MATLIYVDKE NGEPGTRVVA KDGLKLGSGP SIKALDGRSQ VSTPRFGKTF

51   DAPPALPKAT RKALGTVNRA TEKSVKTKGP LKQKQPSFSA KKMTEKTVKA

101  KSSVPASDDA YPEIEKFFPF NPLDFESFDL PEEHQIAHLP LSGVPLMILD

151  EERELEKLFQ LGPPSPVKMP SPPWESNLLQ SPSSILSTLD VELPPVCCDI

201  DI* (SEQ ID NO:4)

A comparison of the amino acid sequence the human PTTG translated product of this open reading frame and that of the rat PTTG protein reveals 77% identity and 89% homology. The cDNAs obtained from these clones represents human homologies of rat PTTG. No other cDNA fragments with higher homology were detected from the library.

Example 11
Tissue Distribution of Human PTTG mRNA

Total RNA was prepared using Trizol Reagent (Gibco-BRL, Gaithersburg, Md.) from normal human pituitary glands (Zoion Research Inc. Worcester, Mass.) and fresh human pituitary tumors collected at surgery and frozen in liquid nitrogen. 20 mg total RNA were used for 1% agarose gel electrophoresis. RNA blots (Clontech, Palo Alto, Calif.) derived from normal adult and fetal tissues as well as from malignant tumor cell lines, were hybridized with radioactively labeled human cDNA fragment containing the complete coding region. The RNA isolated from each cell line was transferred onto a nylon membrane (Amersham, Arlington Heights, Ill.), and hybridized with radioactively labeled probe at 55° C. overnight in 6×SSC, 2×Denhardt's solution, 0.25% SDS. The membranes were washed twice at room temperature for 15 minutes each, and then for 20 minutes at 60° C. in 0.5×SSC, 0.1% SDS, and autoradiographed. The autoradiography was carried out using Kodak BIOMEX-MR film (Eastman Kodak, Rochester, N.Y.) with an intensifying screen. The blots were stripped by washing for 20 minutes in distilled water at 95° C. for subsequent probing.

The results from the Northern blot analysis indicated that PTTG is expressed in liver, but not in brain, lung, and kidney of human fetal tissue. In addition, PTTG is strongly expressed in testis, modestly expressed in thymus, and weakly expressed in colon and small intestine of normal human adult tissue. No expression was detected by Northern analysis in brain, heart, liver, lung, muscle, ovary, placenta, kidney, and pancreas.

The expression of PTTG in several human carcinoma cell lines was also analyzed by Northern blots. In every carcinoma cells examined, PTTG was found highly expressed.

The human tumor cell lines tested are listed in Table 7 below.

TABLE 7

Tested Human Tumor Cell Lines

Promyelocytic leukemia HL-60
Epitheloid carcinoma HeLa cell S3
Chronic myelogenous leukemia K-562
Lymphoblastic leukemia MOLT-4
Burkitt's lymphoma Raji
Colorectal adenocarcinoma SW 480
Lung carcinoma A549
Melanoma G361
Hepatocellular carcinoma Hep 3B
Thyroid carcinoma TC-1
Breast adenocarcinoma MCF-7
Osteogenic sarcoma U2 OS
Placenta choriocarcinoma JAR
Choriocarcinoma JEG-3

Example 12

Human PTTG Expression in Normal Pituitary and Pituitary Tumors

RT-PCR was performed as follows. 5 μg total RNA were treated with 100 U RNase-free DNase I at room temperature for 15 minutes. DNase I was inactivated by incubation at 65° C. for 15 minutes. The sample was then used for reverse transcription using oligo-dT primer and SuperScript II reverse transcriptase (Gibco-BRL, Gaithersburg, Md.). After reverse transcription, the sample was subjected to PCR amplification with PCR SuperMix (Gibco-BRL, Gaithersburg, Md.) using hPTTG-specific primers and human cyclophilin A-specific primers as an internal control.

Northern blot analysis indicated that the level of expression of PTTG is quite low in normal pituitary as well as in pituitary tumors. Therefore, comparative RT-PCR was used to study the expression of PTTG quantitatively in normal pituitary and pituitary tumors. The results of this study showed that in most of pituitary tumors tested, including non-functioning tumors, GH-secreting tumors, and prolactinomas, the expression level of PTTG was higher than that of normal pituitary.

Example 13

Stable Transfection of Human PTTG into NIH 3T3 Cells

The complete coding region of hPTTG cDNA was subcloned in reading frame into the mammalian expression vector pBK-CMV (Stratagene, La Jolla, Calif.), and transfected into NIH 3T3 fibroblast cells by Lipofectamine (Gibco-BRL, Gaithersburg, Md.) according to manufacturer's protocol. 24 hours after transfection, the cells were serially diluted and grown in selection medium containing 1 mg/ml G418 for 2 weeks. Individual clones were isolated and maintained in selection medium. Total RNA was isolated from hPTTG-transfected cell lines as well as from control cells in which blank vector pBK-CMV had been transfected. Northern blot was performed to confirm overexpression of hPTTG in transfected cell lines. These cell lines were used in subsequent cell proliferation assay as well as in vitro and in vivo transformation assay.

Example 14

Cell Proliferation Assay

A cell proliferation assay was performed using the CellTiter 96 non-radioactive cell proliferation assay kit (Promega Medicine, Wis.) according to the manufacturer's protocol. 5,000 cells were seeded in 96well plates and incubated at 37° C. for 24–72 hours. Eight wells were used for each clone in each assay. At each time point, 15 μl of dye solution was added to each well and the cells were incubated at 37° C. for 4 hours. After incubation, 100 μl solubilization/stop solution were added to each well, and the plates incubated overnight at room temperature. The absorbance was determined at 595 nm using an ELISA plate reader.

Control and hPTTG-overexpressing NIH 3T3 cells were used to perform this assay. The results indicated that the growth of cells transfected with the PTTG-expressing vector was suppressed by 30–45% as compared with cells transfected with blank vector. These results clearly show that the PTTG protein inhibits cell proliferation.

Example 15 in vitro and in vivo Transformation Assay (a) In Vitro Transformation Assay

Control and hPTTG-transfected cells were tested for anchorage-independent growth in soft agar. 3 ml of soft agar (20% of 2×DMEM, 50% DMEM, 10% fetal bovine serum, and 20% of 2.5% agar, melted and mixed at 45° C.) were added to 35 mm tissue dishes. 10,000 cells were mixed with 1 ml soft agar and added to each dish, and incubated for 2 weeks until colonies could be counted and photographed.

(b) in vivo Transformation Assay $5 \times 10^5$ cells containing either a blank vector or hPTTG-expressing cells were injected into nude mice. The mice were sacrificed two weeks after injection, and the tumors formed near the injection sites examined.

When the NIH 3T3 cells stably transfected with the PTTG-expressing vector were tested in an anchorage-independent growth assay, these cells caused large colony formation on soft agar, suggesting the transforming ability of PTTG protein.

When the NIH 3T3 cells were injected into nude mice, they caused in vivo tumor formation within 2 weeks after injection. These data indicate that human PTTG, as its rat homologue, is a potent transforming gene.

SUMMARY OF SEQUENCES

SEQ ID NO:1 is the nucleic acid sequence (and the deduced amino acid sequence) of cDNA encoding the rat PTTG protein of the present invention.

SEQ ID NO:2 is the deduced amino acid sequence of the rat PTTG protein of the present invention.

SEQ. ID No:3 is the nucleic acid sequence of cDNA encoding a human PTTG protein of this invention.

SEQ. ID No:4 is the deduced amino acid sequence of a human PTTG protein of this invention.

While the invention has been described in detail with reference to certain preferred embodiments thereof, it should be understood that modifications and variations to the embodiments and exemplary disclosure provided, are within the spirit and scope of the invention as described and claimed in this patent.

What is claimed is:

1. An isolated anti-PTTG antibody, wherein said antibody specifically binds a rat PTTG polypeptide having an amino acid sequence consisting of SEQ ID NO:2.

2. The antibody of claim 1, which is a monoclonal antibody.

3. The antibody of claim 1, which is a polyclonal antibody.

4. A composition, comprising the antibody of claim 1, and a carrier.

5. A method of determining the presence of PTTG polypeptide having an amino acid sequence consisting of SEQ ID NO:2 in a sample, comprising:

contacting a sample with the antibody of claim 1 and allowing the formation of a complex between the antibody and the PTTG polypeptide having an amino acid sequence consisting of SEQ ID NO:2 present in the sample, detecting the presence or absence of an antibody-PTTG polypeptide complex, wherein the presence of an antibody-PTTG peptide complex indicates the presence of PTTG polypeptide having the amino acid sequence consisting of SEQ ID NO:2 in the sample.

6. The method of claim 5 wherein the antibody carries a detectable label, and the detecting step is performed by detecting the presence of the label after separation of the antibody-PTTG polypeptide complex from uncomplexed antibody.

7. A PTTG detection kit, comprising the antibody of claim 1, and instructions for use in detecting the presence of PTTG polypeptides having the amino acid sequence consisting of SEQ ID NO:2.

8. The kit of claim 7, further comprising a PTTG polypeptide having the amino acid sequence consisting of SEQ ID NO:2.

* * * * *